United States Patent
Kelly et al.

(10) Patent No.: US 10,470,705 B2
(45) Date of Patent: Nov. 12, 2019

(54) ESTIMATING VISCERAL FAT BY DUAL-ENERGY X-RAY ABSORPTIOMETRY

(71) Applicant: Hologic, Inc., Bedford, MA (US)

(72) Inventors: Thomas Kelly, Woburn, MA (US); Kevin E. Wilson, Acton, MA (US); Christopher Ruth, Boxford, MA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

(21) Appl. No.: 14/934,514

(22) Filed: Nov. 6, 2015

(65) Prior Publication Data

US 2016/0228057 A1 Aug. 11, 2016

Related U.S. Application Data

(63) Continuation of application No. 12/730,051, filed on Mar. 23, 2010, now Pat. No. 9,179,873, which is a continuation of application No. 10/958,107, filed on Oct. 4, 2004, now Pat. No. 7,725,153.

(51) Int. Cl.
*A61B 5/00* (2006.01)
*A61B 6/00* (2006.01)

(52) U.S. Cl.
CPC .......... *A61B 5/4872* (2013.01); *A61B 5/4869* (2013.01); *A61B 6/482* (2013.01); *A61B 6/4035* (2013.01); *A61B 6/4241* (2013.01); *A61B 6/50* (2013.01); *A61B 6/505* (2013.01)

(58) Field of Classification Search
CPC combination set(s) only.
See application file for complete search history.

(56) References Cited

U.S. PATENT DOCUMENTS

| | | |
|---|---|---|
| 6,198,797 B1 | 3/2001 | Majima et al. |
| 6,215,846 B1 | 4/2001 | Mazess et al. |
| 6,233,473 B1 * | 5/2001 | Shepherd ............... A61B 6/032 378/54 |
| 6,315,447 B1 | 11/2001 | Nord et al. |
| 6,468,209 B1 | 10/2002 | Heymsfield et al. |
| 6,816,564 B2 | 11/2004 | Charles, Jr. et al. |
| 6,969,350 B1 | 11/2005 | Hawthorne et al. |
| 7,444,961 B1 | 11/2008 | Ellis |
| 7,595,043 B2 | 9/2009 | Hedrick et al. |

(Continued)

OTHER PUBLICATIONS

Bertin, Measurement of visceral adipose tissue by DXA combined with anthropometry in obese humans, International Journal of Obesity (2000) 24, 263-270.*

(Continued)

*Primary Examiner* — Katherine L Fernandez
*Assistant Examiner* — Michael S Kellogg
(74) *Attorney, Agent, or Firm* — Kriegsman & Kriegsman

(57) ABSTRACT

A system and a method of using dual-energy absoptiometry to estimate visceral fat metrics and display results, preferably as related to normative data. The process involves deriving x-ray measurements for respective pixel positions related to a two-dimensional projection image of a body slice containing visceral fat as well as subcutaneous fat; at least some of the measurements being dual-energy x-ray measurements, processing the measurements to derive estimates of metrics related to the visceral fat in the slice; and using the resulting estimates.

15 Claims, 6 Drawing Sheets

(56) References Cited

U.S. PATENT DOCUMENTS

| | | |
|---|---|---|
| 7,725,153 B2 | 5/2010 | Kelly et al. |
| 8,792,689 B2 | 7/2014 | Kelly et al. |
| 9,086,356 B2 | 7/2015 | Kelly et al. |
| 9,179,873 B2 | 11/2015 | Kelly et al. |
| 9,865,050 B2 | 1/2018 | Kelly et al. |
| 2001/0053202 A1 | 12/2001 | Mazess et al. |
| 2004/0077088 A1* | 4/2004 | Charles, Jr. ............ A61B 6/032 435/455 |
| 2004/0101086 A1* | 5/2004 | Sabol ................... A61B 5/4872 378/4 |
| 2007/0223795 A1 | 9/2007 | Qing et al. |
| 2010/0168551 A1 | 7/2010 | Moller |
| 2011/0002522 A1 | 1/2011 | Goto et al. |
| 2011/0164798 A1 | 7/2011 | Masumoto |
| 2015/0036910 A1 | 2/2015 | Kelly et al. |
| 2015/0374291 A1 | 12/2015 | Kelly et al. |
| 2018/0189948 A1 | 7/2018 | Kelly et al. |

OTHER PUBLICATIONS

Jensen, Measurement of abdominal and visceral fat with computed tomography and dual-energy x-ray absorptiometry, Am J Clin Nutr 1995;61:274-8.*

Kvist, visceral adipose-tissue volumes derived from measurements with computed tomography in adult men and women: predictive equations. Am J Clin Nutr 1988;48:1351-6.*

Hill et al., "Estimating Abdominal Adipose Tissue with DXA and Anthropometry," Obesity, 15(2): 504-510 (2007).

Specification and drawings of U.S. Appl. No. 15/830,879, inventors Thomas L. Kelly and Kevin E. Wilson, filed Dec. 4, 2017.

Kamel et al., "Usefulness of Anthropometry and DXA in Predicting Intra-abdominal Fat in Obese Men and Women," Obesity Research, 8(1):36-42 (2000).

Kobayashi et al., "A novel method of measuring intra-abdominal fat volume using helical computed tomography," International Journal of Obesity, 26:398-402 (2002).

\* cited by examiner

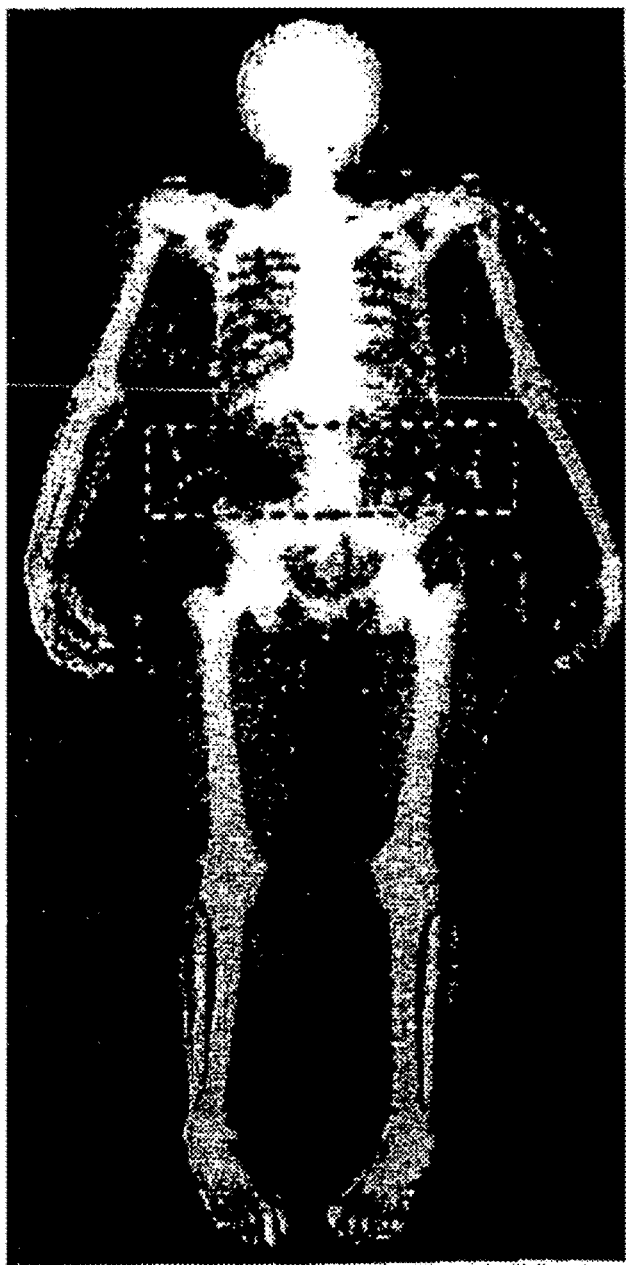
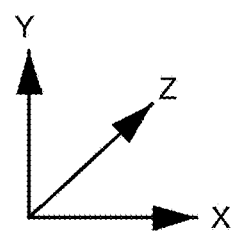
FIG. 2a
FIG. 2b

ESTIMATING VISCERAL FAT BY DUAL-ENERGY X-RAY ABSORPTIOMETRY

RELATED APPLICATIONS

This application is a continuation application of pending U.S. application Ser. No. 12/730,051, filed Mar. 23, 2010, which is a continuation of U.S. application Ser. No. 10/958,107, filed Oct. 4, 2004, now U.S. Pat. No. 7,725,153. Each of the above applications is hereby incorporated by reference.

FIELD

This patent specification pertains to using x-rays to determine internal characteristics of patients or objects, and in a specific implementation pertains to using dual-energy x-ray absorptiometry to determine visceral fat content and to using the results.

BACKGROUND

Although obesity in general can be predictive of morbidities such as coronary artery disease and diabetes, the anatomical distribution of adipose tissue (fat) can be a strong independent predictor of these and other medical conditions and outcomes. For example, overweight subjects with a larger proportion of fat stored as visceral adipose tissue (VAT) are believed to be at a higher risk than similarly overweight individuals with a larger percentage of fat stored \as subcutaneous adipose tissue (SAT). Studies have shown that VAT levels are a predictor of cardiovascular risk factors, e.g., HDL, LDL, triglyceride levels, and hypertension. [1, 2, 3, 4, 10, 11, 12, 13]. (References are identified by numerals in square brackets and are fully cited at the end of this disclosure. The content of the references is hereby incorporated by reference in this patent specification.

Currently, computerized tomography (CT) and magnetic resonance imaging (MRI) are used to measure or estimate VAT by differentiating it from SAT in abdominal cross-sections or slices. [4, 5, 9, 13] Typically, or at least frequently, this measurement is made at the level of the umbilicus, where SAT and VAT volumes typically are identified by an image thresholding algorithm. However, the relatively high cost of both examinations and the high radiation dosage of CT can discourage the use of these techniques as a screening tool for VAT levels. Further, the thresholding method lacks specificity, because areas or volumes above the threshold can have different amounts of % fat, and areas or volumes below the threshold may not be fat-free. Thus, systematic errors can be introduced by assumptions of % fat in areas or volumes above or below the threshold.

Dual-energy x-ray absorptiometry (DXA) exams are widely available, rapid, relatively low dose, and much less costly than CT and MRI exams. Further, DXA is capable of measuring both global and regional fat mass because, for tissue paths that are projected as pixels in the x-ray image, a given dual-energy x-ray measurement pertains to a unique combination of fat and lean mass. [6, 7, 8, 14, 15, 16] However, because DXA is a two-dimensional projection technique, its ability to distinguish between VAT and SAT has been limited.

Because of the predictive and other values of visceral fat as distinguished from general obesity and subcutaneous fat, and the expense and other disadvantages of known techniques for estimating visceral fat, such as CT and MRI, it is believed desirable to find a way to estimate visceral fat more efficiently and effectively, and this patent specification is directed to meeting that need.

SUMMARY

In a non-limiting example, visceral fat is estimated by using projection image DXA measurements of a body slice to estimate parameters related to total fat and lean tissue in the slice and total subcutaneous fat in the slice, and thus indirectly estimate parameters related to visceral fat.

In another non-limiting example, the projection measurements are used to estimate parameters related to subcutaneous fat and parameters related to visceral fat along each of a number of separate x-ray beam paths that correspond to respective pixel values is a projection x-ray image.

The resulting estimates of visceral fat can be used in a variety of ways. They can be displayed alone, or in combination with known or expected ranges of comparable estimates for populations believed to be "normal" or "healthy," which ranges can be matched to the estimates for a patient by some characteristics such as age, sex, and/or ethnicity, or an estimate for a patient can be compared with an estimate for the same patient taken at a different time to assess the change and/or the rate of change, or the estimate can be used in some other way. One non-limiting example is to produce reports similar to those produced for BMD (bone mineral density) in current commercial bone densitometry (DXA) systems but for metrics of visceral fat rather than BMD estimates.

BRIEF DESCRIPTION OF THE DRAWINGS

FIG. 2a illustrates a PA projection image of a patient taken with a DXA system, and FIG. 2b is an enlarged view the portion of the image corresponding to the body slice indicated by a broken line rectangle in FIG. 2a.

DETAILED DESCRIPTION

Figure 1:
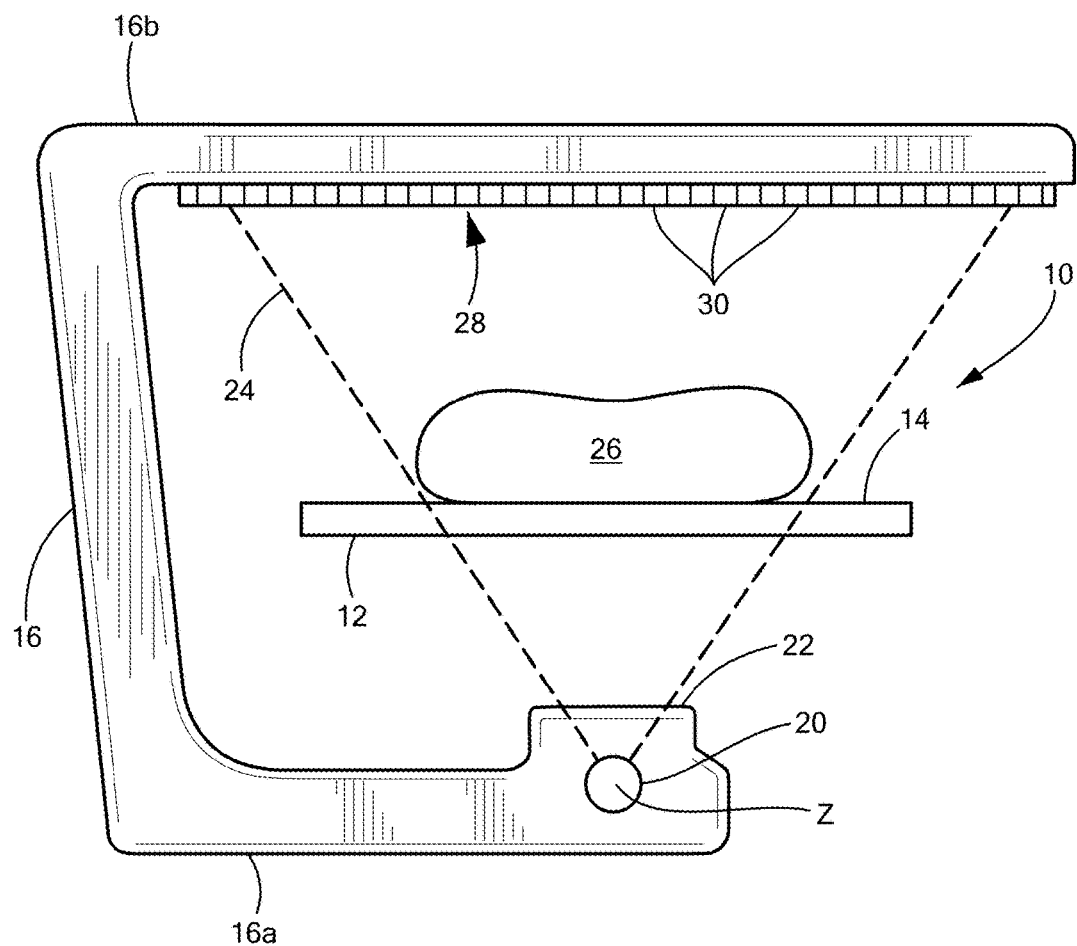
FIG. 1 is a simplified and schematic cross-sectional elevation illustrating a fan-shaped distribution of x-rays in a DXA system in which the visceral fat analysis described herein can be practiced.

Referring to FIG. 1, the new technology can be implemented in a DXA system 10 such as those currently available from the assignee hereof. [15, 16]. System 10 includes a patient table 12 having a support surface 14 that can be considered horizontal and planar in this simplified explanation. FIG. 1 is not to scale, its geometry may not be the same as in current DXA systems, and is used here solely to illustrate and explain certain principles of operation. A human subject 26 is supine on surface 14. The length of the patient is along a horizontal longitudinal axis defined as the y-axis and the patient's arms are spaced from each other along the x-axis. A C-arm 16 has portions 16a and 16b extending below and above table 10, respectively, and is mounted in suitable structure (not shown expressly) for moving at least parallel to the y-axis along the length of patient 26. Lower portion 16a of the C-arm carries an x-ray source 20 that can emit x-rays limited by a collimator 22 into a fan-shaped distribution 24 conforming to a plane perpendicular to the y-axis. The energy range of the x-rays can be relatively wide, to allow for the known DXA dual-energy x-ray measurements, or can be filtered to a narrower range to allow for single energy x-ray measurements. The x-ray distribution can be continuous within the angle thereof or can be made up, or considered to be made up, of individual narrower beams. The x-ray distribution 24 can encompass the entire width of the patient as illustrated, or it can have a narrower angle so the entire patient can be covered only by several passes along the y-axis and the x-ray measurements from the several passes can be combined as is known in the art to simulate the use of a wider fan beam, as typical in current commercial DXA systems. Alternatively, a single, pencil-like beam of x-rays can be used to scan selected regions of the patient's body, e.g. in a raster pattern. The x-rays impinge on x-ray detector 28, which can comprise one or more linear arrays of individual x-ray elements 30, each linear array extending in the x-direction, or a continuous detector where measurements for different positions along the detector can be defined in some manner known in the art, or can be another form of detector of x-rays. C-arm 16 can move at least along the y-axis, or can be maintained at any desired position along that axis. For any one position, or any one unit of incremental travel in the y-direction of arm 16, detector 28 can produce one or several lines of raw x-ray data. Each line can correspond to a row of pixels in a resulting image, which row extends in a direction corresponding to the x-direction. Each line corresponds to a particular position, or range of positions, of the C-arm in its movement along the y-axis and/or a particular linear detector, and comprises a number of individual measurements, each for a respective detector element position in the line, i.e., represents attenuation that the x-rays have suffered in traveling from source 20 to a respective detector element position over a specified time interval. A DXA system takes a higher x-ray energy measurement H and a lower x-ray energy measurement L from each detector element position, and carries out initial processing known in the art to derive, from the raw x-ray data, a set of pixel values for a projection image. Each pixel value comprises a high energy value H and a low energy value L. This can be achieved by rapidly alternating the energy level of the x-rays from source 20 between a higher and a lower range of x-ray energies, for example by rapidly rotating or otherwise moving a suitable filter in or out of the x-rays before they reach patient 26, or by controlling the x-ray tube output, and/or by using an x-ray detector 28 that can discriminate between energy ranges to produce H and L measurements for each pixel position, e.g. by having a low energy and a high energy detector element side-by-side or on top of each other for respective positions in the detector array. The H and L x-ray measurements for the respective pixel positions are computer-processed as known in the art to derive estimates of various parameters, including, if desired, body composition (total mass, fat mass, and lean mass). [8, 15, 16]

A PA projection image taken with a DXA system is illustrated in FIG. 2a. FIG. 2b is an enlarged view of the projection image of the relatively thick slice of the body indicated by the broken line rectangle in FIG. 2a. As suggested by FIGS. 2a and 2b, pixel values are derived from x-ray measurements for a body slice that is along the z-x plane and has a thickness (w) in the y-direction. For example, several hundred pixel values in the x-direction and a several pixel values in the y-direction are derived from the raw x-ray data. Typically but not necessarily, the body slice thickness w along the y-direction is several mm, e.g. 10-15 mm.

Figure 3:
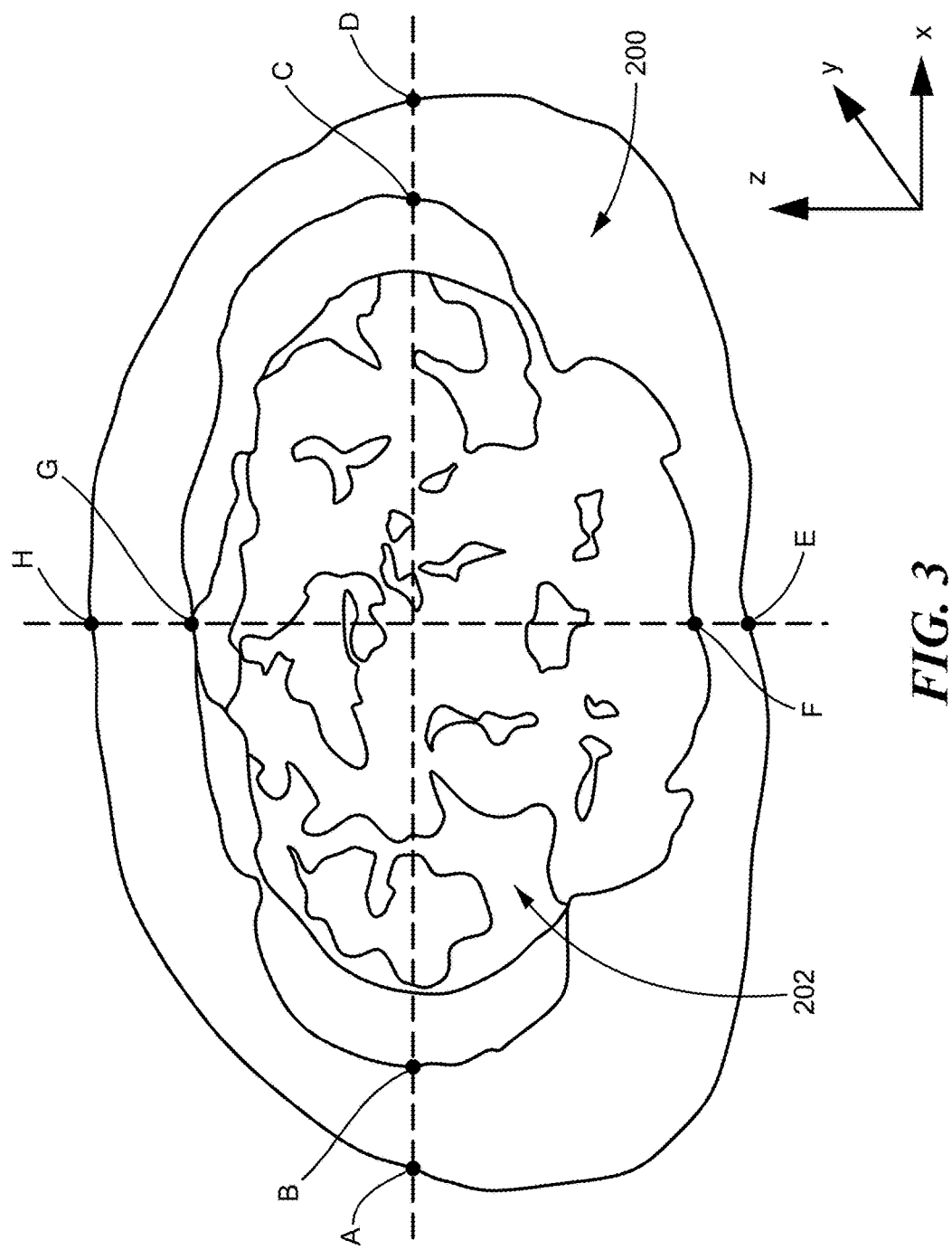
FIG. 3 illustrates a CT cross-sectional image of a body slice.

FIG. 3 illustrates an x-ray image of a section or slice parallel to a z-x plane through the abdominal region of an obese patient taken with a CT system, and shows a ring (non-circular) of subcutaneous adipose tissue (SAT) 200 and regions such as 202 of visceral adipose tissue (VAT) 202. FIG. 3 is used to illustrate certain principles but is not an image taken with DXA equipment. The outline of the slice in the z-x plane can be approximated by an ellipse that has a major axis AD extending from the left to the right side of the illustrated section, and a minor axis EH extending from the bottom to the top of the slice. With that approximation, the estimated total area $\alpha_t$ of the slice is given by $$\alpha_t = \pi(AD/2)(EH/2) \quad \text{Eq. 1}$$

In FIG. 3, the major and minor axes of the inner region that contains the visceral and adipose tissue are BC and FG, respectively, and the estimated area containing the visceral adipose tissue is given by $$\alpha_v = \pi(BC/2)(FG/2) \quad \text{Eq. 2}$$

In DXA practice, AD and BC can be measured with reasonable accuracy from the projection image of the slice in the x-y plane, after accounting for geometric factors due to the use of a fan beam of x-rays and taking into account the source-detector distance and the patient table distance from the source or detector. When the projection image is a PA or AP (taken of a supine patient with an x-ray source below or above the patient), FG is not seen in the image and is not measured directly. However, FG can be estimated, for example by averaging segments AB and CD, which can be measured or estimated reasonably accurately by DXA techniques known in the art, multiplying the average SAT ring thickness (in the x-direction) at the sides of the patient by a scaling factor δ that corrects for the fact that the SAT ring is not perfectly elliptical, and subtracting this from the measured EH value, i.e.

$$FG = EH - \delta(AB+CD)/2 \quad \text{Eq. 3}$$

The scaling factor δ can be estimated from, for example, measurements taken on CT and/or MRI images of similar slices of patients having similar degrees of obesity or other similar physical characteristics.

Alternatively, the distance EH can be estimated from measurements on dual-energy or single energy lateral projection DXA images, in a manner similar to estimating the distance AD from PA or AP DXA images, and the distance FG can be estimated by subtracting the estimated thickness of the SAT ring from EH.

Then, the area $\alpha_v$ of the visceral adipose tissue in the slice that is being examined using DXA techniques is $$\alpha_v = \alpha_t - \alpha_s \quad \text{Eq. 4}$$

Using known techniques, DXA systems measure or estimate total fat mass $M_t(\text{fat})$ and total lean mass $M_t(\text{lean})$ in a body slice. [8, 16, 17] With the estimates identified above, total visceral fat $\text{Fat}_v$ in the slice can be estimated as $$\text{Fat}_v = (M_t(\text{fat}) - \alpha_s w \rho_s) \quad \text{Eq. 5}$$

In Eq. 5, w is an estimate of a thickness of the body slice along the y-axis, and $\rho_s$ is an estimate of density of fat, (which can be assumed based on literature reports or can be measured with known DXA techniques by using the dual-energy x-ray measurements to estimate % fat in the SAT ring (ring 200 in FIG. 2) from pixel values for x-ray beam paths passing only through ring 200 (and skin).

The total lean mass Lean$_v$ in the visceral region of the slice can be estimated similarly, and the percentage fat % Fat$_v$ in the visceral region of the body slice can be calculated as the ratio % Fat$_v$=100(Fat$_v$/Lean$_v$)  Eq. 6

Tissue volumes can be estimated as the tissue area multiplied by the slice thickness w in the y-direction. For example, the visceral adipose volume Volume$_v$ can be estimated as Volume$_v$=π(BC/2)((AB+CD)/4)(δ)(w)  Eq. 7

Figure 4:
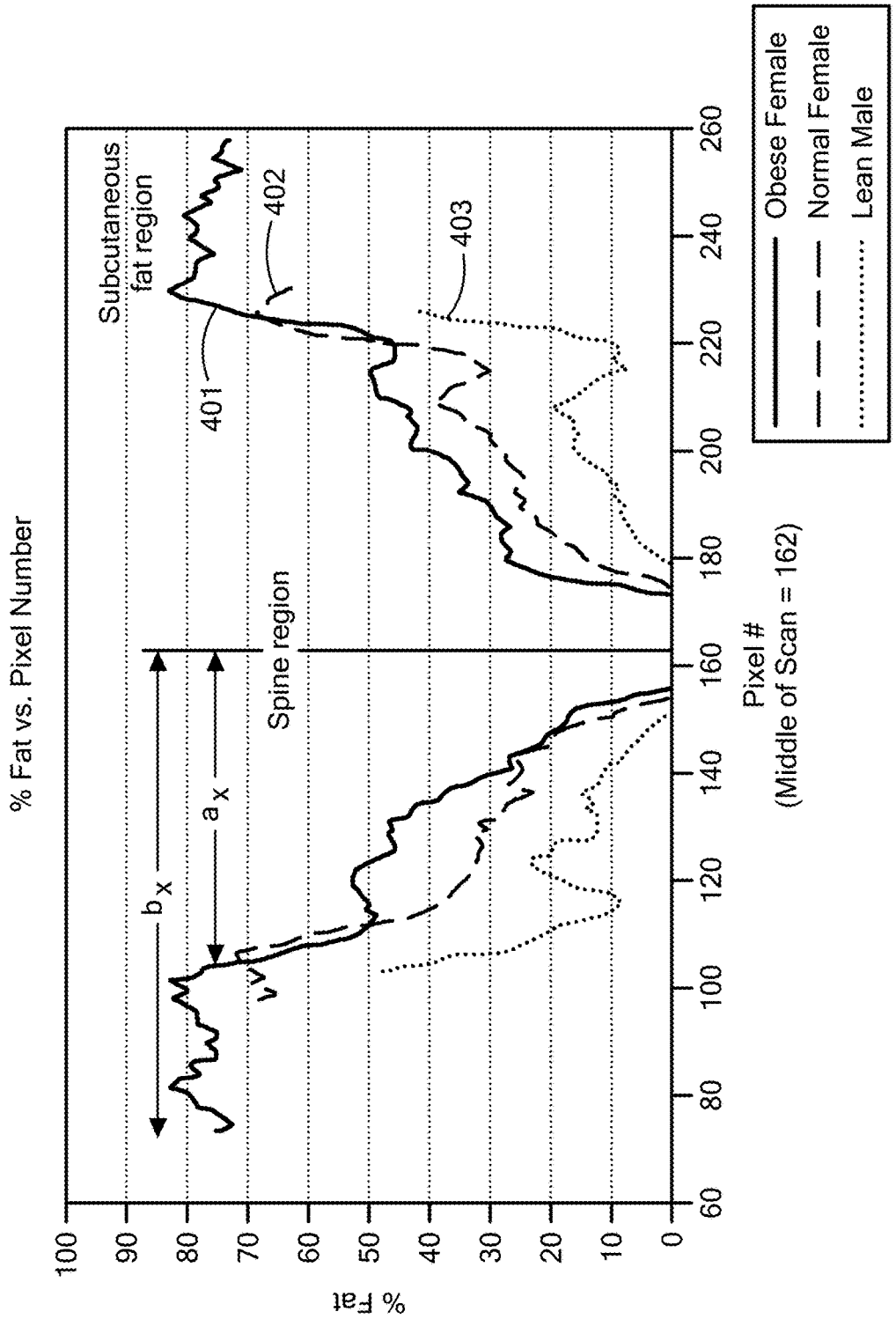
FIG. 4 illustrates graphs of % Fat vs. pixel number for projection images of cross-sectional body slices of three patients taken with a DXA system.

An alternative novel approach is to estimate the visceral fat along each x-ray path from the source (the focal spot of the x-ray tube or another source of x-rays) to each position in the x-ray detector that corresponds to a pixel in the projection x-ray image, for at least some of the image pixels. (The "image" may be in electronic or in visible form.) FIG. 4 illustrates % Fat estimated from PA dual energy x-ray measurements for pixel positions in a DXA image along the x-direction. Curves 401, 402, and 403 are for three different patients. The horizontal axis is pixel number in the DXA image in the x-direction (across the width of the patient). The vertical axis is % Fat, derived as known in the art for PA exams from the H and L raw x-ray data. This is total % Fat for the respective pixel positions, and thus typically includes both SAT and VAT. It is the percentage of fat in the tissue that is along the x-ray beam path from the source to the x-ray detector element(s) that corresponds to a pixel in the image. Curve 401 has shoulders at the left and right extremes (pixels 75-105 and 230-260, approximately) that correspond to SAT. A downwardly extending portion starts from each shoulder toward the middle of the curve (pixels 105-155 and 165-230, approximately). In curve 401, the percentage subcutaneous fat (SAT) is readily seen in the shoulders of the curve, which allows the width of the subcutaneous fat and composition of the subcutaneous fat to be measured or estimated for that region of the body slice. For pixel positions that correspond to the visceral portion of the slice, e.g. pixel position 120, the total % Fat is due to both SAT and VAT. However, the SAT contribution can be estimated by the % Fat at the shoulders of the curve, and removed from the total after an appropriate correction for typical differences in the thickness of SAT at the sides and at the top and bottom of the body slice and geometric corrections such as those discussed above. This can involve a correction similar to the parameter δ in Eq. 3 above, and can be estimated without undue experimentation in a similar manner, e.g. from CT or MRI slices of similar patients or from other sources. Curves 402 and 403 similarly illustrate % Fat for two other patient that have significantly less SAT.

Figure 5:
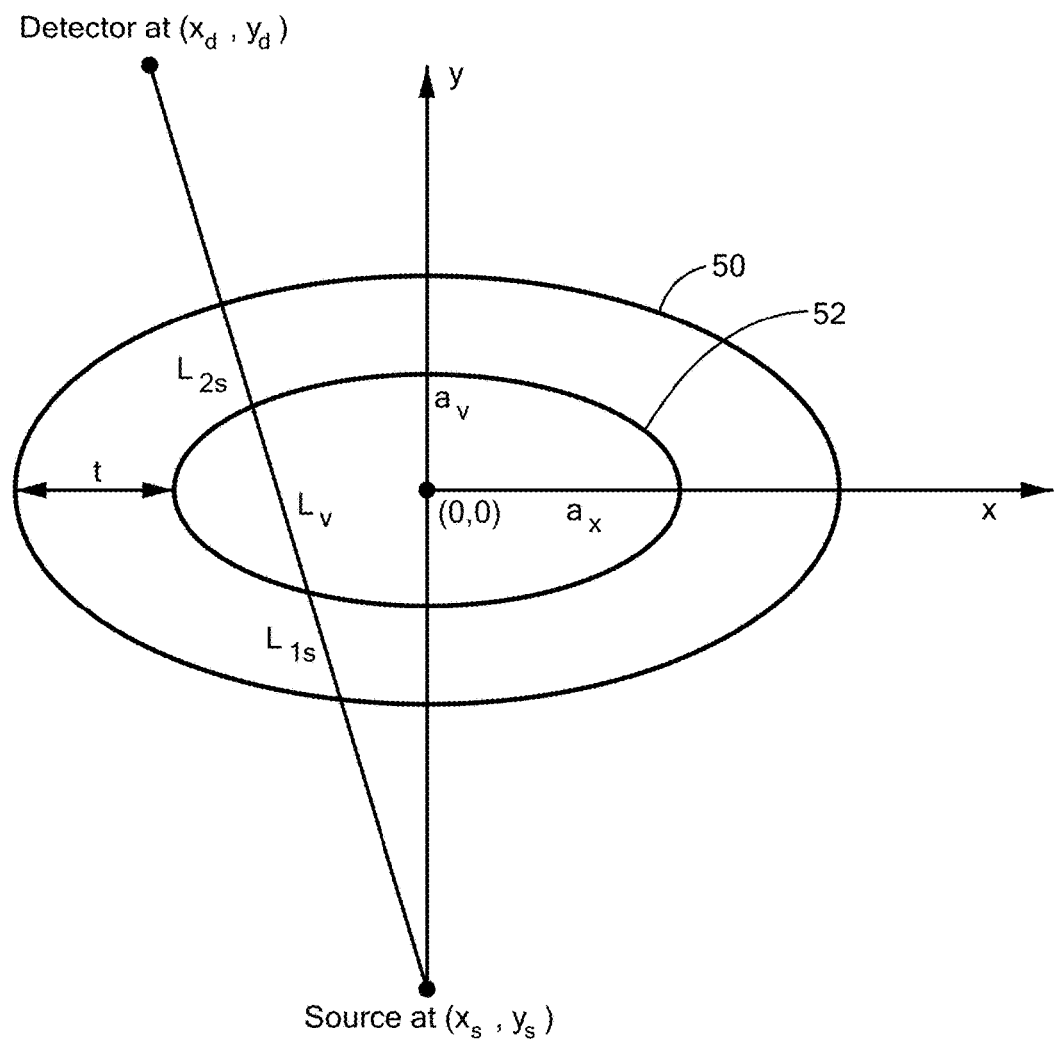
FIG. 5 illustrates geometry related to estimating subcutaneous and visceral fat metrics along individual x-ray energy raypaths.

FIG. 5 illustrates geometry related to estimating VAT and SAT along individual x-ray paths. The outline of the body cross-sectional slice is approximated by an ellipse 50 and the outline of the VAT is approximated by a concentric inner ellipse 52. SAT is between the two ellipses. Let ray i be the line connecting source point ($x_s$, $y_s$) of a fan beam of x-rays to detector point ($x_d$, $y_d$). The total length of intersection ($L_{tot}$) of the line with the concentric ellipses is given by $L_{tot}=L_{1s}+L_{2s}+L_v$  Eq. 8

Where $L_{1s}+L_{2s}=L_s$, the total length of the line i through subcutaneous fat (SAT), and $L_v$ is the length of the same line i through visceral fat (VAT). The pertinent line lengths can be calculated or estimated as discussed below, or in some other way based on known parameters such as the positions of the source and detector relative to ellipses 50 and 52.

The percent fat (% Fat$_{vi}$) in the visceral region for the raypath that is along line i and is from the source focal spot to a detector position that corresponds to a dual energy x-ray measurement for a pixel in the image will be % Fat$_{vi}$=(total % Fat)$_i L_v/L_{tot}$  Eq. 9

The quantity (total % Fat)$_i$ for use in Eq. 9 is estimated from the dual energy x-ray measurements for the raypath using known DXA processing.

Let the inner (visceral) ellipse 52 be defined by the semimajor axes, $a_x$ and $a_y$, and the outer ellipse defined by $b_x$ and $b_y$. The parameters $a_x$ and $b_x$ can be estimated from the profile plot (% Fat vs. pixel #) as illustrated in FIG. 4, with any needed accounting for geometric factors related to using a fan beam of x-rays.

$L_v$ is given by $L_v = \sqrt{(x_2-x_1)^2+(y_2-y_1)^2}$  Eq. 10

Where the parameters on the right-hand side of Eq. 10 are defined in the sets of Equations 11-14 below:

Eq. 11

$x_2=x_s \pm t_2 d_x$  (Eq. 11(1))

$y_2=y_s \pm t_2 d_y$  (Eq. 11(2))

$x_1=x_s \pm t_1 d_x$  (Eq. 11(3))

$y_1=y_s \pm t_1 d_y$  (Eq. 11(4))

Eq. 12

$t_1(-R+\sqrt{P})/F$  (Eq. 12(1))

$t_1(-R-\sqrt{P})/F$  (Eq. 12(2))

Eq. 13

$P=R^2+F-FG$  (Eq. 13(1))

$R=d_x'x_s'+d_y'y_s'$  (Eq. 12(2))

$F=(d_x')^2+(d_y')^2$  (Eq. 13(3))

$G=(x_s')^2+(y_s')^2$  (Eq. 13(4))

Eq. 14

$x_s'=x_s/a_x$  (Eq. 14(1))

$y_s'=y_s/a_y$  (Eq. 14(2))

$d_x'=d_x/a_y$  (Eq. 14(3))

$d_y'=d_y/a_y$  (Eq. 14(4))

$d_x=x_d-x_s$  (Eq. 14(5))

$d_y=y_d-y_s$  (Eq. 14(6))

So $L_v$ is a function of known quantities ($x_s$, $y_s$, $x_d$, $Y_d$) defined in FIG. 4 and estimated quantities ($a_x$, $a_y$) (from Eq. 4, FG=2a$_y$). Since the total intersection length $L_{tot}$ is measured directly, Eq.(9) and Eq.(10) can be used to solve for the % visceral fat for a given ray path through the body.

Another way to more accurately solve for the ellipse parameters $b_x$ and $b_y$ is to use Eq. 10, (also substituting ($b_x$, $b_y$) for ($a_x$, $a_y$) in Eq. 14), in a minimization procedure. Since $L_{tot}$ is measured directly, the parameters ($b_x$, $b_y$) can be varied until the best agreement is attained (for example, using a chi-squared minimization procedure) between measured $L_{tot}$, and $L_{tot}$ calculated from Eq. 13.

When SAT and VAT parameter for individual pixel positions and x-ray paths are estimated as disclosed above, further processing can be carried out to estimate other parameters such as VAT parameters for selected regions of the body slice or for selected organs that are fully or partially in the body slice. For example, the information can be used to evaluate left/right symmetry in the slice in terms of SAT or VAT parameters by separately summing up the estimates for such parameters in the left half and the right half of the slice. As another example, the fat estimates for individual pixels can be used to estimate the percent fat of internal organs such as the liver, by focusing on the x-ray measurements that relate to x-ray beam paths that pass through the liver. Additionally, the local pixel information related to fat estimates can be combined with model assumptions to more accurately estimate visceral fat compared to the more global approach that is explained in detail above in this patent specification. Still further, the local pixel estimates of VAT and SAT parameters can be compared with the overall estimates for the slice obtained through the approach described above in order to improve the modeling and estimates such as the correction factor δ and a similar correction factor used in the approach used in estimating fat parameters for individual pixels.

The results of the processes described above can be in various forms and can be used for a variety of purposes. For example, displays of numerical values of $FAT_v$ can be used in assessing the health, treatment options, or treatments of a patient by a health professional. As another example, such numerical values or estimates derived therefrom can be used as inputs to automated systems for similar assessment or for treatment planning. As yet another example, parameters related to fat metrics can be displayed and recorded or printed as a part of an otherwise typical DXA report including x-ray images and other DXA-produced information for a patient.

Figure 5A:
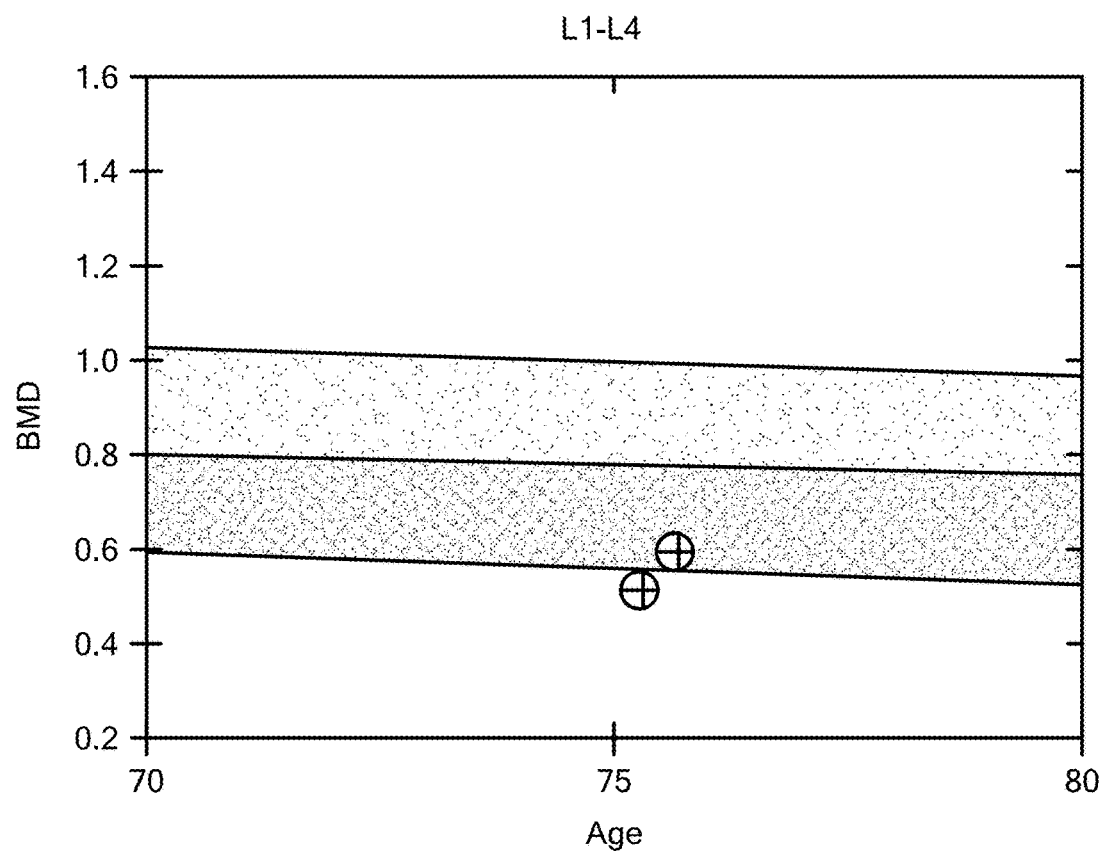
FIG. 5a illustrates a report for BMD estimates from DXA system.

Estimates of visceral fat derived as discussed above can be shown in a variety of ways. They can be displayed alone, or in combination with known or expected ranges of comparable estimates for populations believed to be "normal" or "healthy," which ranges can be matched to the estimates for a patient by some characteristic such as age, sex, and/or ethnicity. The normal or healthy ranges for such characteristics can be obtained by retrospective analysis of already completed studies and/or from new studies to obtain the data. A VAT metric for a patient can be compared with a VAT metric for the same patient taken at a different time to estimate the change and/or the rate of change, for example to see if visceral fat parameters have improved or have deteriorated over some period of time or in relation to some treatment or regimen. Such changes also can be matched to expected or known or estimated ranges to see if the change or rate of change for a patient is statistically significant as distinguished from a change within the precision range of the estimate. The VAT estimates derived as discussed above, or metrics based on such estimates, can be used in other ways as well. One non-limiting example is to produce reports similar to those produced for BMD (bone mineral density) in current commercial bone densitometry (DXA) systems but for metrics of visceral fat (VAT) rather than BMD estimates. An example of a report for typical BMD estimates is illustrated in FIG. 5a; similar reports can be provided for VAT metrics.

Figure 6:
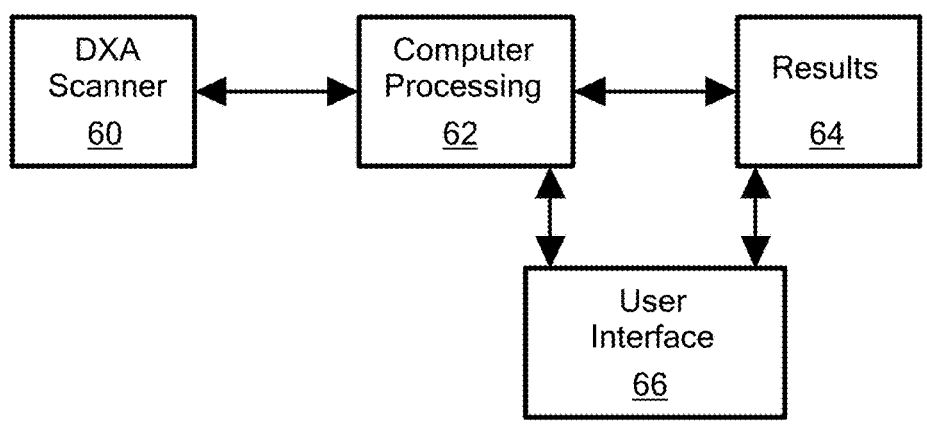
FIG. 6 is a block diagram of a DXA system useful for estimating visceral adipose tissue.

FIG. 6 illustrates in block diagram form a DXA system carrying out the processes described above for estimating VAT. The system can be one of the current DXA systems offered commercially by the assignee [15, 16] programmed to carry out the disclosed processes, using programming that a person of ordinary skill in the art can apply to a particular commercially available DXA system without undue experimentation, given the teachings in this patent specification. A data acquisition system, shown in FIG. 6 as a scanner 60, includes x-ray source 20 and x-ray detector 28 of FIG. 1. Scanner 60 also includes appropriate other components known in the art, such as power and control units, and operates to generate dual energy or single energy x-ray measurements of the selected region or slice of a patient's body. A computer processing unit 62 controls scanner 60 and processes x-ray measurements obtained thereby in accordance with the techniques described above under corresponding programming. A unit 64 displays, prints, stores, and/or sends for further processing or storage, results such as in the form of images as in FIG. 2a and/or 2b, or in the form of curves such as in FIG. 4, or in the form of numeric results indicative or $FAT_v$ or % $FAT_v$, or some other parameter related to visceral fat or other parameter discussed above, including in the immediately preceding paragraph. Units 62 and 64 communicate interactively with a user input unit 66. The actual physical arrangement of system components may differ from the functional illustration in FIG. 6.

The disclosure above is mainly in terms of SAT and VAT of human patients, but it should be clear that its approach is applicable in other fields as well, such as in analysis of other subjects, such as live animals and carcasses. Finally, while a currently preferred embodiment has been described in detail above, it should be clear that a variation that may be currently known or later developed or later made possible by advances in technology also is within the scope of the appended claims and is contemplated by and within the spirit of the detailed disclosure.

REFERENCES

[1] Krotkiewski M, Bjorntorp P, Sjostrom L, Smith U: Impact of obesity on metabolism in men and women. Importance of regional adipose tissue distribution. J Clin Invest. 72(3): 1150-62, 1983.

[2] Nicklas B J, Penninx B W, Ryan A S, Berman D M, Lynch N A, Dennis K E: Visceral adipose tissue cutoffs associated with metabolic risk factors for coronary heart disease in women. Diabetes Care. 26(5):1413-20, 2003.

[3] Morricone L, Donati C, Hassan T, Cioffi P, Caviezel F: Relationship of visceral fat distribution to angiographically assessed coronary artery disease: results in subjects with or without diabetes or impaired glucose tolerance. Nutr Metab Cardiovasc Dis. 12(5):275-83, 2002.

[4] Hayashi T, Boyko E J, Leonetti D L, et. al.: Visceral adiposity and the prevalence of hypertension in Japanese Americans. Circulation. 2003 Oct. 7; 108(14): 1718-23

[5] Kobayashi J, Tadokoro N, Watanabe M, Shinomiya M: A novel method of measuring intra-abdominal fat volume using helical computed tomography. Int J Obes Relat Metab Disord. 26(3):398-402, 2002.

[6] Gronemeyer S A, Steen R G, Kauffman W M, Reddick W E, Glass J O: Fast adipose tissue (FAT) assessment by MR. Magn Reson Imaging. 18(7):815-8, 2000.

[7] Slosman D O, Casez J P, Pichard C, Rochat T, Fery F, Rizzoli R, Bonjour J P, Morabia A, Donath A: Assessment of whole-body composition with dual-energy x-ray absorptiometry. Radiology. 185(2):593-8, 1992.

[8] Kelly T L, Berger N, Richardson T L: DXA body composition: theory and practice. Appl Radiat Isot. 49(5-6):511-3, 1998.

[9] Shepherd, J A, Kelly, T L, Determining Body Composition Using Fan Beam Dual-Energy X-ray Absorptiometry, U.S. Pat. No. 6,233,473,

[10] Kobayashi, J., Tadokoro, N., Watanabe, M., and Shinomiya, M., A novel method of measuring intra-abdominal fat volume using helical computed tomography; International Journal of Obesity (2002) 26, 398-402.

[11] Krotkiewski M, Bjorntorp P, Sjostrom O L, Smith U.; Impact of obesity on metabolism in men and women. Importance of regional adipose tissue distribution. J Clin Invest. 1983, September; 72(3): 1150-62.

[12] Montague, C T and O'Rahilly, S; Perspectives in Diabetes, The Perils of Portliness, Causes and Consequences of Visceral Adiposity, Diabetes, Vol. 49, June 2000, pages 883-888.

[13] Hayashi, T, Boyko, E J, Leonetti, D L; McNeely, M J, Newell-Morris, L, Kahn, S E, Fujimoto, W Y; Visceral Adiposity and the Prevalence of Hypertension in Japanese Americans; American Heart Association, Inc., Circulation. 2003, pages 1718-1723.

[14] Morricone, L.; Donati, C., Hassan, T., Cioffi, P. and Caviezel, F., Relationship of visceral fat distribution to angiographically assessed coronary artery disease: results in subjects with or without diabetes or impaired glucose tolerance; Nutr. Metab, Cardiovasc Dis (2002) a12: 275-283.

[15] Prichard, J. E., Nowson C. a., Stauss, B. J., Carlson J. S., Kaymaker, B. and Wark, J. D., Evaluation of dual energy X-ray absorptiometry as a method of measurement of body fat; European Journal of Clinical Nutrition (1993) 47, 216-228.

[16] Discovery™ brochure, downloaded from Hologic.com webpage on Jul. 19, 2004.

[17] Explorer™ brochure, downloaded from Hologic.com webpage on Jul. 19, 2004.

The invention claimed is:

1. A method of estimating visceral fat content in a body, the method comprising the steps of:
positioning the body in a dual-energy absorptiometry scanner and operating the dual-energy absorptiometry scanner to obtain dual-energy x-ray absorptiometry (DXA) measurements for at least a portion of the body;
with a computer processor, using the DXA measurements to generate a two-dimensional projection image of a slice of the body;
with said computer processor, distinguishing, based solely on the DXA measurements, an area of the two-dimensional projection image that contains subcutaneous fat from an area of the two-dimensional projection image that contains visceral fat, wherein said distinguishing step comprises using the DXA measurements to estimate (a) a major and a minor axis of an ellipse approximating the slice and (b) a portion of the major axis related to subcutaneous fat;
with said computer processor, using the distinguished areas to estimate visceral fat content; and
displaying the estimated visceral fat content on a display.

2. The method as claimed in claim 1 wherein the obtaining step comprises obtaining DXA measurements from an anteroposterior (AP) or a posteroanterior (PA) view of the body.

3. The method as claimed in claim 1 wherein the obtaining step comprises obtaining DXA measurements for only the portion of the body.

4. The method as claimed in claim 1 wherein said displaying step comprises displaying, on the display, the estimated visceral fat content $Fat_v$ in combination with ranges of estimates for a population of other individuals based on one or more selected characteristics including at least one of age and sex.

5. The method as claimed in claim 1 further comprising using the estimated visceral fat content to estimate visceral fat content associated with an individual organ of a patient.

6. A method of estimating visceral fat content in a body, the method comprising the steps of:
positioning the body in a dual-energy absorptiometry scanner and operating the dual-energy absorptiometry scanner to obtain dual-energy x-ray absorptiometry (DXA) measurements for at least a portion of the body;
with a computer processor, using the DXA measurements to generate a two-dimensional projection image of a slice of the body;
with said computer processor, automatically measuring regions of the two-dimensional projection image to determine at least two or more of the following: an area containing subcutaneous fat, an area containing visceral fat, and an area of non-fat material, wherein the step of automatically measuring comprises using the DXA measurements to estimate (a) a major and a minor axis of an ellipse approximating the slice and (b) a portion of the major axis related to subcutaneous fat;
with said computer processor, using the determined areas to estimate visceral fat content; and
displaying the estimated visceral fat content on a display.

7. The method as claimed in claim 6 wherein the obtaining step comprises obtaining DXA measurements from an anteroposterior (AP) or a posteroanterior (PA) view of the body.

8. The method as claimed in claim 6 wherein the obtaining step comprises obtaining DXA measurements for only the portion of the body.

9. The method as claimed in claim 6 wherein said displaying step comprises displaying, on the display, the estimated visceral fat content $Fat_v$ in combination with ranges of estimates for a population of other individuals based on one or more selected characteristics including at least one of age and sex.

10. The method as claimed in claim 6 further comprising using the estimated visceral fat content to estimate visceral fat content associated with an individual organ of a patient.

11. A method of estimating visceral fat content in a body, the method comprising the steps of:
positioning the body in a dual-energy absorptiometry scanner and operating the dual-energy absorptiometry scanner to obtain dual-energy x-ray absorptiometry (DXA) measurements for at least a portion of the body;
with a computer processor, using the DXA measurements to generate a two-dimensional projection image of a slice of the body;
with said computer processor, automatically measuring regions of the two-dimensional projection image to determine an area containing subcutaneous fat, an area containing visceral fat, and an area of non-fat material, wherein the step of automatically measuring comprises using the DXA measurements to estimate (a) a major and a minor axis of an ellipse approximating the slice and (b) a portion of the major axis related to subcutaneous fat;

with said computer processor, using the determined areas to estimate visceral fat content; and displaying the estimated visceral fat content on a display.

12. The method as claimed in claim 11 wherein the obtaining step comprises obtaining DXA measurements from an anteroposterior (AP) or a posteroanterior (PA) view of the body.

13. The method as claimed in claim 11 wherein the obtaining step comprises obtaining DXA measurements for only the portion of the body.

14. The method as claimed in claim 11 wherein said displaying step comprises displaying, on the display, the estimated visceral fat content $Fat_v$ in combination with ranges of estimates for a population of other individuals based on one or more selected characteristics including at least one of age and sex.

15. The method as claimed in claim 11 further comprising using the estimated visceral fat content to estimate visceral fat content associated with an individual organ of a patient.

* * * * *